United States Patent [19]

Peters et al.

[11] Patent Number: Plant 5,585

[45] Date of Patent: Dec. 3, 1985

[54] PLUM TREE, "WUHL"

[76] Inventors: Richard Peters, 4854 E. Butler Ave.; Eric Wuhl, 5480 E. Lane St., both of Fresno, Calif. 93727

[21] Appl. No.: 585,267

[22] Filed: Mar. 1, 1984

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree which is generally similar to the Black Beaut Plum Tree (U.S. Plant Pat. No. 3,617) which it most nearly resembles, bearing purple-skinned, clingstone fruit having redder flesh and a thicker stone than that of the Black Beaut.

1 Drawing Figure

BACKGROUND OF THE NEW VARIETY

The present invention relates to a new and distinct variety of plum tree denominated by the varietal name "WUHL" and broadly characterized by its general similarity to the Black Beaut Plum Tree, which it most nearly resembles, but from which it is distinguished by its extremely large leaves and its regular and productive bearing of purple-skinned, uniformly large fruit having flesh of a redder overall color than that of the Black Beaut, and by its stone which is thicker and has no tendency to crack.

The Black Beaut Plum Tree (U.S. Plant Pat. No. 3,617) is well known as a productive bearer of medium to large fruit having deep purple skin and yellow to red-colored semi-freestone flesh, ripening early in the season. While the Black Beaut has gained a measure of success, it has been recognized that it is deficient in a number of respects, particularly in that its skin is somewhat bitter and its pit is relatively thin and exhibits a tendency to crack. Therefore, it has been recognized that it would be desirable to provide a plum tree bearing fruit which is uniformly large and symmetrically shaped and has a dark skin having no bitter flavor and whose stone has no tendency to crack.

SUMMARY OF THE NEW VARIETY

The instant variety of plum tree is generally characterized by bearing large fruit having purple skin and firm, deep red flesh. In comparison with the Black Beaut variety (U.S. Plant Pat. No. 3,617), the fruit borne by the new variety is more uniformly large, has a deeper red flesh, and a much harder stone having no tendency to crack. Further the skin of the fruit of the new variety has little or no bitterness in comparison to that of the Black Beaut.

The fruit borne by the tree of the new variety is large, having a diameter in the range of from 60 to 65 mm and has firm, crisp, juicy flesh which clings to the stone. The skin of the fruit is Port Wine (Plate 56-L-12) in color and exhibits no bitterness in its flavor. The flesh is Cardinal in color (Plate 5-L-5) and ripens evenly, having very good eating quality. The fruit matures approximately June 15.

The new variety is further particularly characterized by its extremely large leaves and the hardness of its pit, which has little or no tendency to crack. Moreover, the new variety is characterized by its limited self-pollination and the requirement of the intervention on the part of a breeder to effect a sufficient degree of pollination.

BRIEF DESCRIPTION OF THE DRAWING

The accompanying drawing is a color photograph of four mature plums of the subject variety with one of the plums divided to show the flesh and stone characteristics.

DETAILED DESCRIPTION

Referring more specifically to the pomological details of this new and distinct variety of plum tree, the following has been observed under the ecological conditions prevailing in the designated orchard in Fresno County, Calif. All of the color code plate designations are by reference to the Maerz and Paul *Dictionary of Color,* Second Edition, 1950 except where common descriptive color terminology is employed.

TREE

Size: Medium.
Figure: Upright.
Productivity: Productive.
Regularity of bearing: Regular.
Trunk:
- *Diameter in relation to length.*—Medium.
- *Surface characteristics.*—Medium-rough with fine vertical cracks in the bark.

Branches:
- *Size.*—Medium.
- *Surface character.*—Medium rough with vertical cracks.
- *Color.*—Bark — Hudson Seal (Plate 8-A-9); Cracks — Maya (Plate 12-D-10).
- *Lenticels.*—Number — Numerous. Size — Small.

Leaves:
- *Size.*—Large; Length — 135 mm; Width — 65 mm.
- *Shape.*—Oblong-symmetrical; acute at apex and base.
- *Color.*—Upper surface — Shirvan (Plate 24-H-10); Lower surface — Cedar Green (Plate 23-E-6).
- *Marginal form.*—Finely crenate.
- *Petiole.*—Length — 15 to 18 mm; thickness — 2 mm.
- *Stem glands.*—Number — 1 to 3; Arrangement — Irregular; Size — Small; Type — Reniform; Color — Green.
- *Stipules.*—None.

Flower buds:
*Size.*—Small; Shape — Short, Plump; Surface — Glabrous.
Flowers:
*Dates of bloom.*—With Santa Rosa (unpatented).
*Size.*—Small.
*Color.*—White.
*Number of pistils.*—One.
*Number of stamens.*—Numerous.
Pollination: Less self-pollination than Black Beaut (U.S. Plant Pat. No. 3,617).

FRUIT

Maturity: June 15, about three days before Santa Rosa.
*Size.*—Uniformly large; Diameter — 60 to 65 mm; Diameter transverse in suture plane — 57 to 62 mm.; Diameter transverse at right angles to suture plane — 48 to 52 mm.
Form:
*Uniformity.*—Uniform.
*Symmetry.*—Symmetrical.
*Suture.*—Distinct and shallow.
*Ventral surface.*—Slightly raised.
*Stem cavity.*—Acute; 15 mm×25 mm×14 mm deep.
*Base.*—Retuse.
*Apex.*—Retuse.
*Pistil point.*—Indented.
*Stem.*—Length — 22 mm; Caliper — 2.5 mm.
Skin:
*Thickness.*—Thin.
*Texture.*—Tender.
*Tendency to crack.*—None.
*Color.*—Port Wine (Plate 56-L-12).
*Pubescence.*—None.
Flesh:
*Color.*—Cardinal (Plate 5-L-5).
*Color of pit well.*—Mascara (Plate 7-L-8).
*Amygdalin.*—Scant.
*Juice.*—Juicy.
*Flavor.*—Subacid.
*Aroma.*—Wanting.
*Texture.*—Firm and crisp.
*Fibers.*—Moderate, fine and tender.
*Ripening.*—Even.
*Eating quality.*—Very good.
Stone: Cling.
*Fibers.*—Short.
*Size.*—Length — 22 mm; breadth — 17 mm; Thickness — 10 mm.
*Form.*—Lopsided; winged on ventral edge near base; beaked at apex.
*Base.*—Straight.
*Sides.*—Ventral edge — Shallow groove near center; Dorsal edge — Shallow groove throughout.
*Ridges.*—Slightly raised near base.
*Color.*—Topaz (Plate 12-I-8).
*Splitting tendency.*—None.
Use: Fresh market
Keeping quality: Good.
Shipping Quality: Good.

Although the new variety of plum tree possesses the described characteristics under the growing conditions prevailing in Fresno County, in the central portion of the San Joaquin Valley, Calif., it is to be understood that variations of the usual magnitude in characteristics incident to differences in environment, growing conditions, fertilization, irrigation, pruning and pest control are to be expected.

Having thus described and illustrated our new variety of plum tree, what we claim as new and desire to be secured by Letters Patent is:

1. A new and distinct variety of plum tree substantially as shown and described, characterized by its general similarity to the Black Beaut Plum Tree (U.S. Plant Pat. No. 3,617), but differing therefrom in its bearing of uniformly large fruit having redder flesh than that of the Black Beaut which clings over the entire surface of its stone, which is thicker and has less of a tendency to crack than that of the Black Beaut.

* * * * *

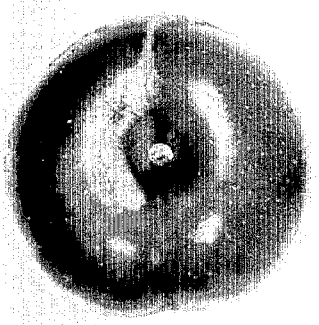
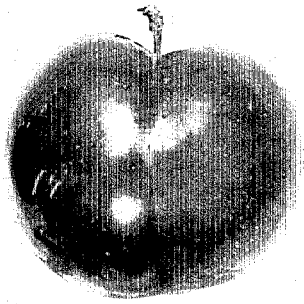
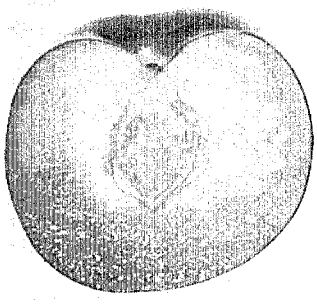
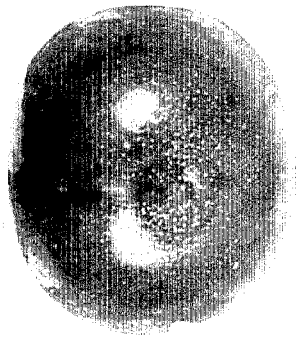

UNITED STATES PATENT AND TRADEMARK OFFICE

CERTIFICATE OF CORRECTION

PATENT NO. : PP 5585

DATED : December 3, 1985

INVENTOR(S) : Richard Peters and Eric Wuhl

It is certified that error appears in the above-identified patent and that said Letters Patent is hereby corrected as shown below:

Column 1, between lines 26 and 27 insert the following:

---ORIGIN AND ASEXUAL
REPRODUCTION OF THE NEW VARIETY

The new variety of plum was discovered by us in 1980 growing as an open-pollinated seedling in an orchard of Mariposa Plum Trees (U.S. Plant Patent No. 111) owned by P & W Farms, a partnership consisting of Eilean Wuhl, Shelly Wuhl, Eric Wuhl and Richard Peters. The orchard was and is located at 1290 South Orange, in the City of Fresno, in the County of Fresno, in the State of California.

We asexually reproduced the new variety in 1981 by grafting onto rootstock in an orchard of plum trees on the Sampson Ranch 30 owned by the Fowler Packing Company and located at the corner of North and Cedar Avenues, in the City of Fresno, in the County of Fresno, in the State of California. Fruit and

UNITED STATES PATENT AND TRADEMARK OFFICE

CERTIFICATE OF CORRECTION

PATENT NO. : PP 5585

DATED : December 3, 1985

INVENTOR(S) : Richard Peters and Eric Wuhl

It is certified that error appears in the above-identified patent and that said Letters Patent is hereby corrected as shown below:

tree characteristics of the trees so reproduced proved identical to that of the originally discovered seedling.---.

Signed and Sealed this

*Twenty-fifth* Day of *February 1986*

[SEAL]

*Attest:*

DONALD J. QUIGG

*Attesting Officer*

*Commissioner of Patents and Trademarks*